United States Patent
Tseng et al.

[19]

[11] Patent Number: 6,159,480
[45] Date of Patent: Dec. 12, 2000

[54] COSMETIC MAKEUP COMPOSITION

[75] Inventors: Chung-Ye Tseng, Warren; Prakash G. Naik-Satam, Bloomfield; Marie E. Yednak, Jamesburg, all of N.J.

[73] Assignee: Neostrata Company, Inc., Princeton, N.J.

[21] Appl. No.: 08/990,460

[22] Filed: Dec. 15, 1997

[51] Int. Cl.[7] .............. A61K 6/00; A61K 7/00; A61K 7/42; A61K 31/74
[52] U.S. Cl. ............ 424/401; 424/59; 424/78.03
[58] Field of Search ................. 424/59, 401, 78.03

[56] References Cited

U.S. PATENT DOCUMENTS

| | | | |
|---|---|---|---|
| 3,879,537 | 4/1975 | Van Scott et al. | 424/311 |
| 3,920,835 | 11/1975 | Van Scott et al. | 424/311 |
| 3,984,566 | 10/1976 | Van Scott et al. | 424/283 |
| 4,105,783 | 8/1978 | Yu et al. | 424/283 |
| 4,197,316 | 4/1980 | Yu et al. | 424/317 |
| 4,234,599 | 11/1980 | Van Scott et al. | 424/279 |
| 4,363,815 | 12/1982 | Yu et al. | 424/274 |
| 4,380,549 | 4/1983 | Van Scott et al. | 424/317 |
| 4,801,445 | 1/1989 | Fukui et al. | 424/69 |
| 4,820,508 | 4/1989 | Wortzman | 424/59 |
| 4,877,805 | 10/1989 | Kligman | 514/381 |
| 5,032,390 | 7/1991 | Iwaya et al. | 424/59 |
| 5,091,171 | 2/1992 | Yu et al. | 424/642 |
| 5,093,109 | 3/1992 | Mausner | 424/63 |
| 5,204,105 | 4/1993 | Mausner | 424/401 |
| 5,250,289 | 10/1993 | Boothroyd et al. | 424/59 |
| 5,385,938 | 1/1995 | Yu et al. | 514/557 |
| 5,389,677 | 2/1995 | Yu et al. | 514/557 |
| 5,560,917 | 10/1996 | Cohen et al. | 424/401 |
| 5,811,413 | 9/1998 | Blank et al. | 514/159 |
| 5,846,551 | 12/1998 | DaCunha et al. | 424/401 |
| 5,871,754 | 2/1999 | Briggs et al. | 424/401 |
| 5,876,736 | 3/1999 | Cohen et al. | 424/401 |
| 5,972,359 | 10/1999 | Sine et al. | 424/401 |
| 6,036,963 | 9/1998 | Weinkauf et al. | 424/401 |

FOREIGN PATENT DOCUMENTS

| | | |
|---|---|---|
| 0 456 459 A2 | 11/1991 | European Pat. Off. . |
| WO 95/04517 | 2/1995 | European Pat. Off. . |
| 0691126A1 | 1/1996 | European Pat. Off. . |
| 0796612A1 | 9/1997 | European Pat. Off. . |
| 0808625A1 | 11/1997 | European Pat. Off. . |

*Primary Examiner*—Thurman K. Page
*Assistant Examiner*—S. Howard
*Attorney, Agent, or Firm*—Foley & Lardner

[57] ABSTRACT

A water-in-silicone cosmetic makeup composition includes a hydroxy acid, a sunscreen agent, a moisturizing agent, an antioxidant, a cosmetically acceptable pigment, an emulsifier, a silicone-containing compound and water. The composition when applied to the skin protects the skin from ultraviolet light exposure, and it reduces the appearance of fine lines and wrinkles. The composition also is highly moisturizing and gentle enough for sensitive skin. Methods of protecting the skin from ultraviolet light exposure and reducing the appearance of fine lines and wrinkles by topically applying this composition, as well as methods of making the emulsified compositions also are disclosed.

33 Claims, No Drawings

COSMETIC MAKEUP COMPOSITION

BACKGROUND OF THE INVENTION

1. Field of the Invention

This application relates to a makeup composition including a water in silicone emulsion containing hydroxyacids, such as alpha hydroxyacids, beta hydroxyacids and/or polyhydroxyacids. The makeup composition, when applied topically to the skin, provides beneficial effects to the skin such as (i) reducing the appearance of lines and wrinkles, (ii) protecting the skin from the harmful effects of the ultraviolet light from the sun, (iii) moisturizing and soothing the skin, and (iv) making the skin attractively colored. This application also relates to methods of topical treatment of the skin to effect such benefits.

2. Description of the Prior Art

Human skin is comprised of two principal components, the outer epidermis and the underlying dermis, which is situated above the subcutaneous adipose or fat tissues. The epidermis consists of four distinct layers: stratum corneum, stratum granulosum, stratum spinosum and stratum basale; in the skin of palms and soles only, there is normally one additional zone called the stratum lucidum between the stratum corneum and the stratum granulosum.

The stratum corneum or horny layer is comprised of numerous flattened dead cells called corneocytes. The granular layer, located below the stratum corneum, contains large granules of keratinous materials. The spinous layer or prickle cell layer is located below the granular layer and composed of keratinocytes. The basal cell layer, located below the spinous layer but above the dermis, is the only principal layer in the epidermis in which living cells normally replicate DNA and divide into daughter cells.

After a basal cell divides, one of the daughter cells migrates into the spinous layer where the cell starts to differentiate as a keratinocyte, wherein synthesis of keratin is initiated. As the keratinocyte continues to move outward and reaches the granular layer, more keratinous materials are synthesized as keratin filaments and large granules. The keratinocyte loses its nucleus in transit through the granular layer and thereupon dies to become a corneocyte without nucleus in the stratum corneum.

Normally, the granular layer is a few cell layers in thickness, and the stratum corneum may be 14–25 cell layers thick. Under normal conditions and in most skin areas, a keratinocyte takes 14 days to move outward from the basal cell layer to the granular layer, and a corneocyte takes 14 days to reach the outermost layer of the stratum corneum to be shed; the total time from basal cell layer to the surface is approximately 28 days. The entire sequence of epidermal terminal differentiation is called keratinization.

The dermis is comprised mainly of collagen, elastic fibers, glycosaminoglycans and proteoglycans including hyaluronic acid, dermatan sulfate and chondroitin sulfate formerly known as mucopolysaccharides. Fibroblasts, the predominant cells of the dermis, synthesize collagen, elastic fibers, proteoglycans and glycosaminoglycans. Collagen makes up approximately 77%, elastic fibers account for about 2%, and glycosaminoglycans constitute around 0.2% of the dry weight of the dermis. Collagen provides the tensile strength of and elastic fibers give resilience to the dermis. The glycosaminoglycans binds water to form a gelatinous mass between collagen and elastic fibers, which acts as a lubricant and shock absorber for the dermis during movement of the skin.

Several factors affect human skin and result cutaneous aging to form wrinkles, sagging and loss of firmness and elasticity. These factors include internal factors and external factors. Cutaneous aging, while having epidermal concomitants, seems to involve primarily dermal and subcutaneous changes, and is caused by (a) internal factors alone, as in intrinsic aging and (b) external factors, as in extrinsic aging. Intrinsic aging also is known as natural or chronologic aging, and extrinsic aging often is called photoaging. "Photodamage" implies skin damage caused by chronic sun exposure. These terms may be described as follows.

Intrinsic aging of skin, in sun-protected skin of the upper arm and abdomen, is an inherent degenerative process that occurs in all humans and is due to declining physiologic functions and capacities. This degenerative process may include qualitative and quantitative skin changes and also includes diminished or defective synthesis of collagen and elastic fibers, and proteoglycans and glycosaminoglycans in the dermis. Signs of intrinsic aging include progressive thinning of skin, deepening of skin lines and fine wrinkles, lusterless skin surface, and loss of skin elasticity and recoilability. Although intrinsic aging of living creatures is neither reversible nor preventable, modification and improvement of skin signs associated with such aging process can be achieved through topical management.

Extrinsic aging of skin is a distinctive process caused by external factors which include sunlight, radiation, air pollution, wind, cold, dampness, heat, chemicals, smoke and cigarette smoking. Photoaging of skin may be defined as destructive cutaneous changes caused by chronic exposure to sunlight. Signs of photoaging on the face and back of hands include coarse and deepened wrinkles due to changes and degeneration of collagen and elastic fibers; marked loss of elasticity and recoilability; leathery skin surface and skin lesions with abnormal pigmentation and increased numbers of age spots, pigmented spots, blotches and nodules. Histologically, the qualities and quantities of elastin and collagen tissues are changed. Normal elastin in tissues is replaced by abnormal elastin characterized as solar elastosis, and the normal collagen fibers are decreased.

Photodamage of skin, also called solar damage, may be defined as cutaneous damage caused by chronic exposure to solar radiation and is associated with development of neoplastic lesions. Skin disorders caused by photodamage include pre-malignant lesions, basal cell carcinomas, squamous cell carcinomas and malignant melanomas.

There are numerous products available today that report to ameliorate some of the signs of cutaneous aging. For example, there are a number of sunscreen patents related to treating aging skin. U.S. Pat. No. 5,093,109 describes the use of titanium dioxide as a sunscreen which also contains antioxidants, emulsifiers, thickeners and colorants. U.S. Pat. No. 5,204,105 describes the use of plant and yeast extracts, vitamins E & C to improve elasticity, the use of silicones to improve firmness and the use of sunscreens to protect the skin from the sun. A number of cosmetic compositions are known that contain titanium dioxide either alone, or in combination with a silicone compound for various uses. See, U.S. Pat. Nos. 4,801,445, 4,820,508, 5,032,390 and 5,250,289.

Other known compositions containing sunscreens together with free radical scavengers are described in, for example, U.S. Pat. No. 5,093,109. These compositions, however, generally are oil in water emulsions containing ascorbyl palmitate, which rapidly falls apart in such an emulsion. U.S. Pat. No. 5,560,917 describes a composition containing a sunscreen agent, a free radical scavenger and a cosmetically acceptable pigment.

There also are numerous descriptions in the literature of the use of alpha hydroxyacids and polyhydroxyacids for treating various skin disorders. U.S. Pat. No. 3,879,537 describes the use of topical compositions containing an alpha hydroxyacid to alleviate the symptoms of ichthyosis. U.S. Pat. No. 3,920,835 describes the use of topical compositions containing an alpha hydroxyacid to alleviate the symptoms of acne. U.S. Pat. No. 3,984,566 describes the use of topical compositions containing an alpha hydroxyacid to improve the symptoms of dandruff.

Other document, for example, U.S. Pat. Nos. 4,105,783, 4,197,316 and 4,380,549 describe the use of topical compositions containing an alpha hydroxyacid to alleviate or improve the symptoms of dry skin. In addition, U.S. Pat. No. 4,234,599 describes the use of topical compositions containing an alpha hydroxyacid to alleviate the symptoms of actinic or nonactinic skin keratoses. Moreover, U.S. Pat. No. 4,363,815 describes the use of topical compositions containing certain alpha hydroxyacids to improve skin conditions characterized by inflammation or disturbed keratinization.

Recently issued U.S. Pat. Nos. 5,385,938 and 5,389,677 describe the use of compositions containing glycolic acid for topical treatment of skin wrinkles. Albert M. Kligman also described in U.S. Pat. No. 4,877,805 that photoaging or sun damaged skin includes loss of collagen fibers, abnormal changes in elastic fibers and deterioration of small blood vessels in the dermis of the skin. The dermal components which make up the fibers of the dermis become smaller and sparser with increasing age, usually in sundamaged facial skin. There is a great loss of collagen fibers resulting in looseness and easy stretchability of the skin; elastic fibers become abnormal so that the skin does not promptly snap back after being stretched. Kligman disclosed the use of retin-A to treat photoaged or sundamaged skin.

These known compositions, are not always effective against the external effects of sunlight and the internal effects caused by intrinsic aging.

SUMMARY OF THE INVENTION

There exists a need for a single cosmetic composition that is effective not only against the external effects of sunlight but the internal effects caused by intrinsic aging. It is therefore an object of the present invention to provide such a composition. It is an additional object of the present invention to provide a composition that achieves the objectives described above, and at the same time colors the skin attractively.

In accordance with these and additional objects of the invention, there is provided a water in silicone emulsified cosmetic makeup composition including:

1) At least one hydroxy acid selected from polyhydroxy acid, alpha hydroxy acid, beta hydroxyacid, keto carboxylic acid and related compounds;
2) Sunscreen agent(s);
3) Moisturizing agent(s);
4) Antioxidant(s);
5) Cosmetically acceptable pigment(s);
6) Silicone-containing compound(s); and
7) water.

In accordance with additional objects of the invention, there are provided methods of reducing the appearance of lines and wrinkles, protecting the skin from harmful effects of ultraviolet light, moisturizing, soothing and firming the skin and attractively coloring the skin comprising topically applying the above water in silicone emulsified cosmetic makeup composition in a cosmetically effective amount to achieve the aforementioned effects.

In accordance with additional objects of the invention, there are provided methods of making a water in silicone emulsified cosmetic makeup composition by:

A) dissolving in water at least one hydroxy acid selected from polyhydroxy acid, alpha hydroxy acid, beta hydroxyacid, keto carboxylic acid and related compounds in water and neutralizing to a pH of above 3.0 to provide phase A;

B) providing an aqueous mixture containing at least one moisturizing agent, heating the mixture, and adding this mixture to phase A to provide phase AB;

C) mixing at least one sunscreen agent, at least one antioxidant, at least one surfactant and at least one silicone-containing compound at room temperature, followed by heating and homogenizing the mixture to provide phase C;

D) providing a mixture containing at least one sunscreen agent and at least one cosmetically acceptable pigment, homogenizing the mixture to provide phase D;

E) mixing phases C) and D) together and homogenize until uniform to provide mixture CD;

F) slowly adding phase AB to phase CD to produce phase F;

G) adding to phase F a mixture containing parabens; and

H) adding additional cosmetically acceptable pigments to provide the appropriate color.

Additional objects and advantages of the invention will be set forth in part in the description that follows, and in part will be obvious from the description, or may be learned by practice of the invention. The objects and the advantages of this invention may be realized and obtained by means of the compositions and methods particularly pointed out in the appended claims.

DETAILED DESCRIPTION OF PREFERRED EMBODIMENT

Throughout this description, the expressions "alpha hydroxy acid," "AHA" and "2-hydroxycarboxylic acid" are used synonymously and denote any known alpha hydroxyacid useful in treating skin disorders, including those described in, inter alia, U.S. Pat. No. 5,091,171, the disclosure of which is incorporated herein by reference in its entirety. Throughout this description, the expression "polyhydroxy acid" denotes any of the known poly hydroxyacids reported as being useful in treating skin disorders, including poly hydroxyacids disclosed in U.S. Pat. No. 5,091,171. Throughout this description, the expression "beta hydroxyacid" denotes any beta hydroxyacid useful in treating skin disorders. Throughout this description, the expression "keto carboxylic acid" denotes any of the known keto carboxylic acids reported as being useful in treating skin disorders, including those disclosed in U.S. Pat. No. 5,091,171. Throughout this description, the expression "related compound" refers to compounds that are structurally and functionally similar to alpha hydroxyacids and polyhydroxy acids such as those related compounds disclosed in U.S. Pat. No. 5,091,171.

For convenience, the alpha hydroxyacids, polyhydroxy acids and related compounds which may be used in accordance with this invention may be classified into three groups, namely (1) 2-hydroxycarboxylic acids, (2) 2-ketocarboxylic acids and esters thereof, and (3) other related compounds. The related compounds may include hydroxycarboxylic acids with the hydroxyl group at any position other than position 2, for example position 3, position 4 or position 5, as well as cyclic hydroxycarboxylic acids (e.g., ascorbic acid and quinic acid), and also may include ketocarboxylic acids and esters thereof. Preferred related compounds include 3-hydroxycarboxylic acids, and 2-ketocarboxylic acids and esters thereof.

Group 1

The first group comprises organic carboxylic acids in which one hydroxy group is attached to the 2 position carbon atom of the acid. The generic structure of such 2-hydroxycarboxylic acids may be represented as follows:

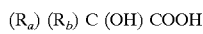

(R$_a$) (R$_b$) C (OH) COOH

Where R$_a$ and R$_b$ may be the same or different and are independently selected from H, F, Cl, Br, alkyl, aralkyl or aryl group of saturated or unsaturated, isomeric or non-isomeric, straight or branched chain or cyclic form, having 1 to 29 carbon atoms, and in addition R$_a$ and R$_b$ may carry OH, CHO, COOH and alkoxy group having 1 to 9 carbon atoms. In addition, the hydrogen atoms of R$_a$ and/or R$_b$ may be substituted by a nonfunctional element selected from Cl, Br, I, S, F, or a radical such as a low alkyl or alkoxy group, saturated or unsaturated, having 1 to 9 carbon atoms. The alpha hydroxy acids of Group 1 may be present as a free acid or lactone form, or in a salt form with an organic base or an inorganic alkali. The alpha hydroxy acids of Group 1 may exist as stereoisomers as D, L, and DL forms when R$_a$ and R$_b$ are not identical.

Typical alkyl, aralkyl and aryl groups for R$_a$ and R$_b$ include methyl, ethyl, propyl, isopropyl, butyl, pentyl, octyl, decyl, dodecyl, hexadecyl, benzyl, and phenyl, etc. Alpha hydroxy acids of Group 1 may be further divided into subgroups comprising (1) alkyl hydroxycarboxylic acids, (2) aralkyl and aryl hydroxycarboxylic acids, (3) polyhydroxy acids, and (4) hydroxy-polycarboxylic acids. The following are representative alpha hydroxy acids in each subgroup.

(1) Alkyl Hydroxycarboxylic Acids
1. 2-Hydroxyethanoic acid (Glycolic acid, hydroxyacetic acid) (H) (H) C (OH) COOH
2. 2-Hydroxypropanoic acid (Lactic acid) (CH$_3$) (H) C (OH) COOH
3. 2-Methyl 2-hydroxypropanoic acid (Methyllactic acid) (CH$_3$) (CH$_3$) C (OH) COOH
4. 2-Hydroxybutanoic acid (C$_2$H$_5$) (H) C (OH) COOH
5. 2-Hydroxypentanoic acid (C$_3$H$_7$) (H) C (OH) COOH
6. 2-Hydroxyhexanoic acid (C$_4$H$_9$) (H) C (OH) COOH
7. 2-Hydroxyheptanoic acid (C$_5$H$_{11}$) (H) C (OH) COOH
8. 2-Hydroxyoctanoic acid (C$_6$H$_{13}$) (H) C (OH) COOH
9. 2-Hydroxynonanoic acid (C$_7$H$_{15}$) (H) C (OH) COOH
10. 2-Hydroxydecanoic acid (C$_8$H$_{17}$) (H) C (OH) COOH
11. 2-Hydroxyundecanoic acid (C$_9$H$_{19}$) (H) C (OH) COOH
12. 2-Hydroxydodecanoic acid (Alpha hydroxylauric acid) (C$_{10}$H$_{21}$) (H) C (OH) COOH
13. 2-Hydroxytetradecanoic acid (Alpha hydroxymyristic acid) (C$_{12}$H$_{25}$) (H) C (OH) COOH
14. 2-Hydroxyhexadecanoic acid (Alpha hydroxypalmitic acid) (C$_{14}$H$_{29}$) (H) C (OH) COOH
15. 2-Hydroxyoctadecanoic acid (Alpha hydroxystearic acid) (C$_{16}$H$_{33}$) (H) C (OH) COOH
16. 2-Hydroxyeicosanoic acid (Alpha hydroxyarachidonic acid) (C$_{18}$H$_{37}$) (H) C (OH) COOH
17. 2-Hydroxytetraeicosanoic acid (Cerebronic acid) (C$_{22}$H$_{45}$) (H) C (OH) COOH
18. 2-Hydroxytetraeicosenoic acid (Alpha hydroxynervonic acid) (C$_{22}$H$_{43}$) (H) C (OH) COOH (2) Aralkyl And Aryl 2-Hydroxycarboxylic Acids
1. 2-Phenyl 2-hydroxyethanoic acid (Mandelic acid) (C$_6$H$_5$) (H) C (OH) COOH
2. 2,2-Diphenyl 2-hydroxyethanoic acid (Benzilic acid) (C$_6$H$_5$) (C$_6$H$_5$) C (OH) COOH
3. 3-Phenyl 2-hydroxypropanoic acid (Phenyllactic acid) (C$_6$H$_5$CH$_2$) (H) C (OH) COOH
4. 2-Phenyl 2-methyl 2-hydroxyethanoic acid (Atrolactic acid) (C$_6$H$_5$) (CH$_3$) C (OH) COOH
5. 2-(4'-Hydroxyphenyl) 2-hydroxyethanoic acid (4-Hydroxymandelic acid) (HO—C$_6$H$_4$) (H) C (OH) COOH
6. 2-(4'-Chlorophenyl) 2-hydroxyethanoic acid (4-Chloromandelic acid) (Cl—C$_6$H$_4$) (H) C (OH) COOH
7. 2-(3'-Hydroxy-4'-methoxyphenyl) 2-hydroxyethanoic acid (3-Hydroxy-4-methoxymandelic acid) (HO—, CH$_3$O—C$_6$H$_3$) (H) C (OH) COOH
8. 2-(4'-Hydroxy-3'-methoxyphenyl) 2-hydroxyethanoic acid (4-Hydroxy-3-methoxymandelic acid) (HO—, CH$_3$O—C$_6$H$_3$) (H) C (OH) COOH
9. 3-(2'-Hydroxyphenyl) 2-hydroxypropanoic acid [3-(2'Hydroxyphenyl) lactic acid] (HO—C$_6$H$_4$—CH$_2$) (H) C (OH) COOH
10. 3-(4'-Hydroxyphenyl) 2-hydroxypropanoic acid [3-(4'-Hydroxyphenyl) lactic acid] (HO—C$_6$H$_4$—CH$_2$) (H) C (OH) COOH
11. 2-(3',4'-Dihydroxyphenyl) 2-hydroxyethanoic acid (3,4-Dihydroxymandelic acid) (HO—,HO—C$_6$H$_3$) (H) C (OH) COOH (3) Polyhydroxy Acids
1. 2,3-Dihydroxypropanoic acid (Glyceric acid) (HOCH$_2$) (H) C (OH) COOH
2. 2,3,4-Trihydroxybutanoic acid (Isomers; erythronic acid, threonic acid) (HOCH$_2$ HOCH) (H) C (OH) COOH
3. 2,3,4,5-Tetrahydroxypentanoic acid (Isomers; ribonic acid, arabinoic acid, xylonic acid, lyxonic acid) (HOCH$_2$ HOCH HOCH) (H) C (OH) COOH
4. 2,3,4,5,6-Pentahydroxyhexanoic acid (Isomers; allonic acid, altronic acid, gluconic acid, mannoic acid, gulonic acid, idonic acid, galactonic acid, talonic acid) (HOCH$_2$ HOCH HOCH HOCH) (H) C (OH) COOH
5. 2,3,4,5,6,7-Hexahydroxyheptanoic acid (Isomers; glucoheptonic acid, galactoheptonic acid etc.) (HOCH$_2$ HOCH HOCH HOCH HOCH) (H) C (OH) COOH (4) Hydroxy-polycarboxylic Acids
1. 2-Hydroxypropane-1,3-dioic acid (Tartronic acid) (HOOC) (H) C (OH) COOH
2. 2-Hydroxybutane-1,4-dioic acid (Malic acid) (HOOC CH$_2$) (H) C (OH) COOH
3. 2,3-Dihydroxybutane-1,4-dioic acid (Tartaric acid) (HOOC HOCH) (H) C (OH) COOH
4. 2-Hydroxy-2-carboxypentane-1,5-dioic acid (Citric acid) (HOOC CH$_2$)$_2$ C (OH) COOH
5. 2,3,4,5-Tetrahydroxyhexane-1,6-dioic acid (Isomers; saccharic acid, mucic acid etc.) HOOC (CHOH)$_4$ COOH The alpha hydroxy acids of Group 1 may be present in forms other than the acid, such as, for example, salts or lactones. Typical lactone forms which may be used in accordance with this invention include, for example, gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

Group 2

The second group, which comprises compounds related to the alpha hydroxyacids of Group 1, includes organic carboxylic acids in which one keto group is attached to position 2 carbon atom of the acid. These compounds are referred to herein as keto carboxylic acids or 2-ketoacids. The generic structure of such 2-ketoacids, or alpha ketoacid may be represented as follows:

$$(R_c) \text{ CO COO } (R_d)$$

wherein $R_c$ and $R_d$ can be the same or different and are each selected from H, alkyl, aralkyl or aryl group of saturated or unsaturated, isomeric or non-isomeric, straight or branched chain or cyclic form, having 1 to 29 carbon atoms, and in addition $R_c$ may carry F, Cl, Br, I, OH, CHO, COOH and alkoxy group having 1 to 9 carbon atoms. In addition, the hydrogen atoms of $R_c$ and/or $R_d$ may be substituted by a nonfunctional element selected from Cl, Br, I, S, F, or a radical such as a low alkyl or alkoxy group, saturated or unsaturated, having 1 to 9 carbon atoms. The alpha ketoacids may be present as a free acid or an ester form, or in a salt form with an organic base or an inorganic alkali. The typical alkyl, aralkyl and aryl groups for $R_c$ and $R_d$ include methyl, ethyl, propyl, 2-propyl, butyl, pentyl, hexyl, octyl, dodecyl, hexadecyl, benzyl and phenyl.

The ester form of the above-mentioned 2-ketoacids also is therapeutically effective for alleviating the signs and symptoms of cutaneous aging including intrinsic and extrinsic aging. For example, methyl 2-ketopropanoate and ethyl 2-ketopropanoate are therapeutically very effective. While the mechanism of action of these 2-ketoacids is not known, it is believed that the ester form of the 2-ketocarboxylic acid is chemically and/or biochemically very reactive, and a free 2-ketoacid may be released in the skin after penetration through the stratum corneum of the skin.

The representative 2-ketoacids and their esters of the second group are listed below:
1. 2-Ketoethanoic acid (Glyoxylic acid) (H) CO COOH
2. Methyl 2-ketoethanoate (H) CO COOCH$_3$
3. 2-Ketopropanoic acid (Pyruvic acid) CH$_3$ CO COOH
4. Methyl 2-ketopropanoate (Methyl pyruvate) CH$_3$ CO COOCH$_3$
5. Ethyl 2-ketopropanoate (Ethyl pyruvate) CH$_3$ CO COOC$_2$H$_5$
6. Propyl 2-ketopropanoate (Propyl pyruvate) CH$_3$ CO COOC$_3$H$_7$
7. 2-Phenyl-2-ketoethanoic acid (Benzoylformic acid) C$_6$H$_5$ CO COOH
8. Methyl 2-phenyl-2-ketoethanoate (Methyl benzoylformate) C$_6$H$_5$ CO COOCH$_3$
9. Ethyl 2-phenyl-2-ketoethanoate (Ethyl benzoylformate) C$_6$H$_5$ CO COOC$_2$H$_5$
10. 3-Phenyl-2-ketopropanoic acid (Phenylpyruvic acid) C$_6$H$_5$CH$_2$ CO COOH
11. Methyl 3-phenyl-2-ketopropanoate (Methyl phenylpyruvate) C$_6$H$_5$CH$_2$ CO COOCH$_3$
12. Ethyl 3-phenyl-2-ketopropanoate (Ethyl phenylpyruvate) C$_6$H$_5$CH$_2$ CO COOC$_2$H$_5$
13. 2-ketobutanoic acid C$_2$H$_5$CO COOH
14. 2-Ketopentanoic acid C$_3$H$_7$ CO COOH
15. 2-Ketohexanoic acid C$_4$H$_9$ CO COOH
16. 2-Ketoheptanoic acid C$_5$H$_{11}$ CO COOH
17. 2-Ketooctanoic acid C$_6$H$_{13}$CO COOH
18. 2-Ketododecanoic acid C$_{10}$H$_{21}$ CO COOH
19. Methyl 2-ketooctanoate C$_6$H$_{14}$ CO COOCH$_3$
Group 3

The third group, which also comprises related compounds, includes, inter alia, hydroxycarboxylic acids where the hydroxy is at a position other than position 2, and cyclic hydroxycarboxylic acids which are useful for topical application to improve signs of aging skin and the cutaneous appendages. The members of this group, which are more conveniently identified by name than by generic structures, include ascorbic acid, quinic acid, isocitric acid, tropic acid (2-phenyl 3-hydroxypropanoic acid), trethocanic acid, 3-chlorolactic acid, citramalic acid, agaricic acid, aleuritic acid, pantoic acid, lactobionic acid and hexulosonic acid.
Group 4

The fourth group includes beta hydroxyacids in which a hydroxy group is attached to the beta carbon atom of the acid. The generic structure of such beta hydroxyacids may be represented as follows:

$$R_e(CR_fOH)_m(CH_2)COOH$$

where $R_e$, $R_f$ are selected from the group consisting of hydrogen, alkyl, aralkyl and aryl, where said alkyl, aralkyl or aryl can be saturated or unsaturated, straight, branched or cyclic, and have from 1–25 carbon atoms. In addition, the hydrogen atoms of $R_e$ and/or $R_f$ may be substituted by a nonfunctional element selected from Cl, Br, I, S, F, or a radical such as a low alkyl or alkoxy group, saturated or unsaturated, having 1 to 9 carbon atoms. In the generic structure above, m preferably is an integer of from 1 to 9. The beta hydroxyacids may be present as a free acid or an ester form, or in a salt form with an organic base or an inorganic alkali. Preferably, $R_e$ and $R_f$ are selected from methyl, ethyl, propyl, 2-propyl, butyl, pentyl, hexyl, octyl, dodecyl, hexadecyl, benzyl and phenyl.

The alpha hydroxyacids, polyhyrdoxyacids, 2-ketoacids, beta hydroxyacids and related compounds are used in a cosmetically effective amount to reduce or alleviate the signs of fine lines and wrinkles. Preferably, these compounds are used in an additive amount within the range of from about 0.1 to about 25% by weight, based on the total weight of the composition. "Additive amount," as it is used herein denotes the total amount of component used in the composition, such as the total amount of alpha hydroxyacids, polyhydroxyacids, 2-ketoacids and related compounds used. More preferably, these compounds are used in an amount within the range of from about 2 to about 10% by weight and more preferably, from about 4 to about 8% by weight.

Preferably, the alpha hydroxyacids, polyhydroxyacids, 2-ketoacids and related compounds are neutralized with an appropriate base to a pH of more than about 3, more preferably more than about 3.5 and most preferably, to a pH of about 3.8. Any cosmetically acceptable base can be used to neutralize the alpha hydroxyacids, polyhydroxyacids, 2-ketoacids and related compounds. Preferably, the base is selected from sodium hydroxide or ammonium hydroxide or triethanoloamine and most preferably, the base is ammonium hydroxide. Those skilled in the art are capable of determining an effective amount of alpha hydroxyacids, polyhydroxyacids, 2-ketoacids and related compound together with an acceptable quantity of base using the guidelines provided herein.

Throughout this description, the expression "sunscreen agent" denotes known sunscreen agents that are useful in absorbing, screening or preventing ultraviolet rays from penetrating the skin. Preferably, the sunscreen agent is titanium dioxide or zinc oxide, and more preferably the sunscreen agent is coated with a polymeric material or other cosmetically acceptable coating. Preferred sunscreen agents can be selected from microfine titanium dioxide coated with aluminum hydroxide and stearic acid (aluminum stearate), cosmetic grade titanium dioxide coated with C9–C15 polyfluoroalkyl phosphate, polymer coated zinc oxide, octyl dimethyl PABA, PABA and its esters, benzophenone-3, octyl salicylate, menthyl anthranilate, and phenylbenzimidazole sulfonic acid.

The sunscreen agent can be used in any effective amount that will prevent or inhibit ultraviolet rays from penetrating the skin. Specifically, the sunscreen agent is provided in an amount to provide a sunscreen protection factor of at least 8, more preferably, at least 15, and even more preferably, at least 30. Preferably, the sunscreen agent is used in an amount within the range of from about 0.1% to about 50% by weight, based on the total weight of the composition. More preferably, the sunscreen agent is used in an additive amount within the range of from about 0.1 to about 20% by weight, and most preferably, within the range of from about 6 to about 16% by weight.

Throughout this description, the expression "moisturizing agent(s)" denotes any agents that provide a moisturizing effect to the skin, e.g., any known humectant. Any moisturizing agent can be used in any moisturizing effective amount. Preferably, the moisturizing agent is selected from glycerin, butylene glycol or their derivatives such as 1,3-butylene glycol and glycerine, propylene glycol, sorbitol, sodium PCA, glucam E-10, glucam E-20, and POE (7–26) glycerine. Those skilled in the art recognize useful moisturizing agents that can be used in the present invention, using the guidelines provided herein. Preferably, the moisturizing agent is used in an amount within the range of from about 0.1 to about 10% by weight, based on the total weight of the composition, more preferably, from about 0.1 to about 5% by weight, and most preferably, from about 1 to about 5% by weight.

Any antioxidant(s) can be used in any effective amount to prepare the cosmetic composition of the invention. Preferably, the antioxidant is a natural antioxidant such as a Vitamin E derivative, e.g., Vitamin E linoleate, Vitamin E, Vitamin E POE succinate, Vitamin E acetate, ascorbic acid, ascorbyl palmitate and ascorbyl-PMG. The antioxidant useful in the invention can be used in an additive amount within the range of from about 0.1 to about 10% by weight, based on the total weight of the composition, preferably, from about 0.1 to about 5% by weight, and more preferably, from about 0.5 to about 1% by weight.

Throughout this description, the expression "cosmetically acceptable pigment" denotes any pigments that are useful in providing color to a cosmetic composition, and which do not adversely affect the skin. Any cosmetically acceptable pigment can be used in any effective amount to prepare the cosmetic composition of the invention. Preferably, the cosmetically acceptable pigment is an inorganic pigment such as iron oxide (yellow, red and black), manganese oxide, and F D & C Aluminum Lakes. Zinc oxide and titanium dioxide, although described herein as being useful sunscreen agents, can also be used within the context of the present invention as a pigment. The pigments, although useable in raw form as an iron oxide, preferably are coated with a polymeric coating, more preferably, the pigments are polyfluoroalkyl coated inorganic pigments. The pigments useful in the invention can be used in an additive amount within the range of from about 0.1 to about 25% by weight, based on the total weight of the composition, preferably, from about 1 to about 20% by weight, and more preferably, from about 2 to about 15% by weight.

The water in silicone emulsified cosmetic makeup composition of the present invention also includes silicone-containing compounds. Any known cosmetically silicone-containing compound can be used in a cosmetically effective amount. Preferably, the silicone-containing compound(s) is selected from cyclomethicone, dimethicone and derivatives thereof, such as cyclomethicone/quaternium-18 hectorite, cyclomethicone polyol, dimethicone polyol, and cetyl dimethicone copolyol and combinations thereof. Those skilled in the art will appreciate that the silicone-containing compound (s) also can function as an emulsifier, especially when the silicone-containing compound is selected from dimethicone polyol or cetyl dimethicone copolyol. Silica also is preferably used in the present invention. More preferably, the silicone-containing compounds are selected from cyclomethicone, dimethicone, phenyl methicone, phenyl dimethicone and phenyl trimethicone.

The silicone-containing compounds preferably are used in an amount within the range of from about 1 to about 50% by weight, based on the total weight of the composition. More preferably, the silicone-containing compounds are used in an additive amount within the range of from about 5 to about 30% by weight, and most preferably, from about 10 to about 25% by weight.

The balance of the composition is comprised of customary additives selected from auxiliaries, filler, emulsifiers, surfactants, solvents, buffers, emollients and other cosmetically acceptable carriers and fillers, and water. Other conventional additives can be used in the present invention, including antioxidants, dispersants, humectants, thickeners and preservatives. Water typically is deionized water, and the amount of water typically is anywhere from about 10 to about 80 by weight, based on the total weight of the composition, preferably from about 15 to about 75% by weight, and most preferably from about 20 to about 40% by weight. The amount of conventional additives typically ranges from about 0 to about 20% by weight, based on the total weight of the composition, preferably from about 1 to about 15% by weight, and most preferably from about 4 to about 10% by weight.

As an emulsion, the emulsified composition of the present invention includes an oil phase and an aqueous phase. The oil phase preferably is present in an amount within the range of from about 1 to about 75% by weight, based on the total weight of the composition, more preferably, from about 5 to about 60% by weight, and most preferably from about 40 to about 60% by weight.

Emulsifiers can be used to assist in preparing the emulsified cosmetic makeup composition of the invention. Any cosmetically acceptable emulsifier can be used in an amount that provides the desired emulsifying effect. Preferably, the emulsifier is selected from known soaps and surfactants, more preferably, the emulsifier is selected from stearic acid, sorbitan sesquioleate, polyethylene glycol (PEG)-30 dipolyhydroxystearate, lecithin, magnesium stearate, and derivatives and mixtures thereof. The emulsifiers preferably are used in an additive amount within the range of from about 0.5 to about 30% by weight, based on the total weight of the composition, more preferably, from about 1 to about 12% by weight and most preferably from about 4 to about 8% by weight.

Those skilled in the art are capable of selecting particular ingredients for use in the present composition, and they are capable of determining an appropriate amount of ingredient to provide a water in silicone emulsified cosmetic makeup composition.

A particularly preferred composition for reducing the appearance of fine lines and wrinkles, moisturizing and protecting the skin from the harmful effects of sunlight includes a water in silicone emulsion containing about 0.1 to 25 weight % ultrafine titanium dioxide, from about 0.1 to 25 weight % of microfine zinc oxide, from about 0.1 to 25 weight % of a mixture of gluconolactone (as a polyhydroxy acid) and glycolic acid (as an alpha hydroxyacid) neutralized to a pH of 3.80 with any base, preferably ammonium hydroxide, from about 0.1 to 5 weight % of vitamin E derivative, preferably vitamin E linoleate, from about 0.1 to 5 weight % of a moisturizing agent, preferably glycerin and from about 0.1 to 25% of a blend of cosmetically acceptable pigments, preferably polyfluoroalkyl coated inorganic pigments.

Even more preferred embodiments of the invention include the use of microfine titanium dioxide coated with aluminum hydroxide and stearic acid (aluminum stearate), cosmetic grade titanium dioxide coated with C9–C15 polyfluoroalkyl phosphate, and polymer coated zinc oxide as sunscreen agents, Gluconolactone and/or glycolic acid as the hydroxy acid(s), Vitamin E linoleate as a natural antioxidant, glycerin and/or butylene glycol as moisturizing agent(s) (i.e., humectant(s)), and cosmetically acceptable iron oxide pigments.

To prepare an emulsified cosmetic composition in accordance with the present invention, at least one hydroxy acid or related compound first is dissolved in a solution prepared from ethanol, water, propylene glycol, butylene glycol, acetone or other pharmaceutically acceptable vehicle, and then neutralized with an appropriate base. The emulsified cosmetic composition can be prepared as follows:

A) dissolving in water at least one hydroxy acid selected from polyhydroxy acid, alpha hydroxy acid, beta hydroxy acid, keto carboxylic acid and related compounds in water and neutralizing with an appropriate base to a pH of above 3.0 to provide phase A;

B) providing an aqueous mixture containing at least one moisturizing agent, heating the mixture, and adding this mixture to phase A to provide phase AB;

C) mixing at least one sunscreen agent, at least one antioxidant, at least one emulsifier and at least one silicone-containing compound at room temperature, followed by heating and homogenizing the mixture to provide phase C;

D) providing a mixture containing at least one sunscreen agent and at least one cosmetically acceptable pigment, homogenizing the mixture to provide phase D;

E) mixing phases C) and D) together and homogenize until uniform to provide mixture CD;

F) slowly adding phase AB to phase CD to produce phase F;

G) adding to phase F a mixture containing parabens; and

H) adding additional cosmetically acceptable pigments to provide the appropriate color.

In step A), the hydroxyacid preferably is gluconolactone and/or glycolic acid. In step B), the moisturizing agent(s) preferably are 1,3-butylene glycol and glycerine and the mixture is heated to a temperature within the range of from about 35–50° C., preferably from about 40–45° C. The mixture of step B) preferably is stirred for about 10 minutes prior to addition to phase A). It is preferred to mix the ingredients of phase C) together at room temperature, whereby the pigment preferably is titanium dioxide, the emulsifier preferably is sorbitan sesquioleate and lecithin, the antioxidant preferably is Vitamin E linoleate and the silicone-containing compound preferably is selected from cyclomethicone and dimethicone. The components of phase C) preferably are mixed together at room temperature, followed by heating and homogenizing for about 30 minutes or until the mixture is substantially homogeneous.

In preparing the emulsified cosmetic composition of the invention, it is preferred to use only a portion of the cosmetically acceptable pigment to prepare phase D), more preferably, use only 90% of the pigment, most preferably 80%. The remaining pigment may be added later in step H) to adjust the color of the cosmetic composition. The mixture of phase D) preferably is homogenized for about 30 minutes until uniform. Phase D) then is added to phase C) and the mixture of CD) is homogenized for about 30 minutes until uniform. In step F), phase AB) is slowly added to phase CD) with slow speed mixing. A mixture containing parabens then is added to the mixture of AB) and CD) with high mixing and mixed for at least 5 minutes, and the color of the final emulsion is adjusted using the remaining pigment from step D).

The present invention also encompasses a method of reducing the appearance of fine lines and wrinkles, protecting the skin from ultraviolet radiation exposure, moisturizing and soothing the skin comprising topically applying a water in silicone emulsified cosmetic makeup composition of the invention to an area of the skin in need thereof. Preferably, the composition is applied to areas of the skin that are typically exposed to ultraviolet radiation, such as the arms, hands, face, feet, legs, chest, buttocks and abdomen, although the composition of the invention can be applied to any area of skin. The composition of the present invention preferably is applied on a daily basis, and more preferably, twice daily in order to achieve the appropriate effects. Preferably, the composition of the present invention is applied twice daily for a period of at least 2 months, preferably at least 5 months, and most preferably more than 8 months to achieve a reduction in the appearance of fine lines and wrinkles. The rate and duration of application can be varied, however, depending on the concentration of effective ingredients. Skilled artisans are capable of designing a suitable application regimen to provide the requisite fine line and wrinkle reducing effect as well as ultraviolet exposure reducing effect using the guidelines provided herein.

The following are illustrative examples of formulations and compositions according to this invention. Although the examples utilize only selected compounds and formulations, it should be understood that the following examples are illustrative and not limited. Therefore, any of the known alpha hydroxyacids, polyhydroxy acids, beta hydroxyacids, keto carboxylic acids, related compounds, moisturizing agents, antioxidants, silicone-containing compounds, emulsifiers, pigments and sunscreen agents may be substituted according to the teachings of this invention in the following examples.

EXAMPLES

A preferred makeup composition and its method of manufacture is described below.

| PHASE | INGREDIENTS | % |
|---|---|---|
| A | DI WATER | 20.900 |
|   | GLUCONOLACTONE | 4.000 |
|   | AMMONIUM HYDROXIDE | 0.600 |
|   | SODIUM CHLORIDE | 1.000 |
| B | 1,3-BUTYLENE GLYCOL | 3.000 |
|   | PEG-30 DIPOLYHYDROXYSTEARATE | 1.000 |
|   | N-ETHYL N-SOYAMORPHOLINIUM ETHOSULFATE/WATER | 1.000 |
|   | GLYCERINE | 2.000 |
| C | TITANIUM DIOXIDE/ISOSTEARYL NEOPENTANOATE/ STEARIC ACID/ALUMINUM | 10.000 |

-continued

| PHASE | INGREDIENTS | % |
|---|---|---|
|  | HYDROXIDE |  |
|  | POLYMETHYL METHACRYLATE | 2.000 |
|  | CYCLOMETHICONE/DIMETHICONE COPOLYOL | 5.000 |
|  | NYLON-12 | 2.500 |
|  | ISODODECANE | 3.500 |
|  | ISOHEXADECANE | 3.000 |
|  | VITAMIN E LINOLEATE | 0.500 |
|  | SORBITAN SESQUIOLEATE | 1.000 |
|  | CETYL DIMETHICONE COPOLYOL | 1.500 |
|  | CYCLOMETHICONE/QUATERNIUM-18 HECTORITE/ PROPYLENE CARBONATE | 5.000 |
|  | LECITHIN | 0.500 |
|  | MAGNESIUM STEARATE | 0.500 |
|  | POLYETHYLENE | 2.000 |
|  | SILICA | 1.500 |
|  | SILK POWDER | 1.000 |
| D | TITANIUM DIOXIDE | 3.000 |
|  | CYCLOMETHICONE | 15.000 |
|  | TALC | 0.500 |
|  | IRON OXIDE YELLOW | 5.330 |
|  | IRON OXIDE RED | 1.420 |
|  | IRON OXIDE BLACK | 0.750 |
| E | PHENOXYETHANOL/ISOPROPYL PARABEN/ ISOBUTYL PARABEN/BUTYL PARABEN | 1.000 |
|  |  | 100.00 |

The above cream makeup composition was prepared as follows, whereby the amounts of ingredients are indicated above in weight percent.

1) Gluconolactone was dissolved in water, stirred for about 3 hours, and the pH was adjusted to 3.80 with addition of ammonium hydroxide. Sodium chloride then was added to the solution to prepare phase A.

2) The ingredients for phase B then were mixed together and heated to 40–45° C. The heated mixture was stirred for about 10 minutes and added to phase A above to provide phase AB.

3) The ingredients of phase C were mixed together in a separate container at room temperature, followed by heating and homogenizing for 30 minutes until uniform to provide phase C.

4) In a container separate from that used to prepare phase C), and using only 80% of the iron oxide pigment, the ingredients of phase D (less the 20% of iron oxide pigment) were mixed together and homogenized for 30 minutes until uniform to provide phase D.

5) Phase D then was added to phase C to prepare phase CD), and phase CD) was homogenized for 30 minutes until uniform.

6) The ingredients of phase AB then were slowly added to phase CD with slow speed mixing.

7) The ingredients of phase E then were added to the emulsion of step 6), and the emulsion was homomixed at high speed for 5 minutes. The color of the resulting emulsified cosmetic composition was adjusted and matched using the remaining 20% of iron oxide pigments from step 4) to prepare a water in silicone emulsified cosmetic makeup composition.

The water in silicone emulsified cosmetic makeup composition then can be applied to various places on the body, preferably on the face, arms and hands, and used as both an effective sunscreen and as a composition effective in removing or alleviating the signs of aging such as fine lines and wrinkles.

It will be apparent to those skilled in the art that various modifications and variations can be made to the compositions of matter and methods of this invention. Thus, it is intended that the present invention covers such modifications and variations.

What is claimed is:

1. A water in silicone emulsified cosmetic makeup composition comprising:
   1) a least one hydroxy acid selected from the group consisting of polyhydroxy acids, alpha hydroxy acids, beta hydroxyacids, keto carboxylic acids and related compounds;
   2) sunscreen agent(s);
   3) moisturizing agent(s);
   4) antioxidant(s);
   5) cosmetically acceptable pigment(s);
   6) silicone-containing compound(s); and
   7) water.

2. The makeup composition as claimed in claim 1, wherein at least one hydroxy acid is gluconolactone.

3. The makeup composition as claimed in claim 1, wherein the alpha hydroxy acid is glycolic acid.

4. The makeup composition as claimed in claim 1, wherein the sunscreen agent is comprised of ultrafine particles of titanium dioxide coated with aluminum hydroxide and stearic acid.

5. The makeup composition as claimed in claim 1, wherein the sunscreen agent is comprised of ultrafine particles of zinc oxide coated with polymeric materials.

6. The makeup composition as claimed in claim 1, wherein the moisturizing agent(s) is selected from glycerin or butylene glycol.

7. The makeup composition as claimed in claim 1, wherein the antioxidant is vitamin E linoleate or vitamin E acetate.

8. The makeup composition as claimed in claim 1, wherein the cosmetically acceptable pigment is at least one C9–C15 polyfluoroalkyl treated iron oxide.

9. The makeup composition as claimed in claim 4, wherein the sunscreen agent is present in an amount sufficient to provide a sun protection factor of at least 15.

10. The makeup composition as claimed in claim 1, further comprising an emulsifier.

11. A method of reducing the appearance of fine lines and wrinkles, protecting the skin from harmful effects of ultraviolet light, moisturizing and soothing the skin comprising topically applying a water in silicone emulsified cosmetic makeup composition in a cosmetically effective amount and for an effective period of time, wherein said water in silicone emulsified cosmetic makeup composition comprises:
   1) at least one hydroxy acid selected from the group consisting of polyhydroxy acids, alpha hydroxy acids, beta hydroxyacids, keto carboxylic acids and related compounds;
   2) sunscreen agent(s);
   3) moisturizing agent(s);
   4) antioxidant(s);
   5) cosmetically acceptable pigment(s);
   6) silicone-containing compound(s); and
   7) water.

12. A method of making a water in silicone emulsified cosmetic makeup composition as claimed in claim 1, comprising:
   A) dissolving in water at least one hydroxy acid selected from the group consisting of polyhydroxy acids, alpha hydroxy acids, beta hydroxy acids, keto carboxylic acids and related compounds in water and neutralizing the solution to a pH of above 3.0 to provide phase A;

B) providing an aqueous mixture containing at least one moisturizing agent, heating the mixture, and adding this mixture to phase A to provide phase AB;

C) mixing in a separate container from phase AB, at least one sunscreen agent, at least one antioxidant, at least one surfactant and at least one silicone-containing compound at room temperature, followed by heating and homogenizing the mixture to provide phase C;

D) mixing in a container separate from phase AB and phase C, at least one sunscreen agent and at least one cosmetically acceptable pigment, and homogenizing the mixture to provide phase D;

E) mixing phases C) and D) together and homogenizing the mixture until uniform to provide phase CD;

F) slowly adding phase AB to phase CD to produce phase F;

G) adding to phase F a mixture containing parabens; and

H) optionally adding an additional cosmetically acceptable pigment to adjust the color of said cosmetic makeup composition.

13. The method as claimed in claim 12, wherein at least one hydroxy acid is gluconolactone.

14. The method as claimed in claim 12, wherein the alpha hydroxy acid is glycolic acid.

15. The method as claimed in claim 12, wherein the sunscreen agent is comprised of ultrafine particles of titanium dioxide coated with aluminum hydroxide and stearic acid.

16. The method as claimed in claim 12, wherein the sunscreen agent is comprised of ultrafine particles of zinc oxide coated with polymeric materials.

17. The method as claimed in claim 12, wherein the moisturizing agent(s) is selected from glycerin or butylene glycol.

18. The method as claimed in claim 12, wherein the antioxidant is vitamin E linoleate.

19. The method as claimed in claim 12, wherein the cosmetically acceptable pigment is at least one C9–C15 polyfluoroalkyl treated iron oxide.

20. The method as claimed in claim 12, further comprising adding an emulsifier.

21. The makeup composition as claimed in claim 10, wherein said emulsifier is one or more emulsifiers selected from the group consisting of dimethicone copolyol, stearic acid, sorbitan sesquioleate, polyethylene glycol dipolyhydroxystearate, lectithin, magnesium stearate, cetyl dimethicone copolyol, and derivatives thereof.

22. The makeup composition as claimed in claim 1, wherein said silicon-containing compound(s) is one or more compounds selected from the group consisting of cyclomethicone, dimethicone, cyclomethicone/quaternium-18 hectorite, cyclomethicone polyol, dimethicone polyol, cetyl dimethicone copolyol, silica, phenyl methicone, phenyl dimethicone, and phenyl trimethicone and derivatives thereof.

23. The method as claimed in claim 20, wherein said emulsifier is one or more emulsifiers selected from the group consisting of dimethicone copolyol, stearic acid, sorbitan sesquioleate, polyethylene glycol dipolyhydroxystearate, lectithin, magnesium stearate, cetyl dimethicone copolyol, and derivatives thereof.

24. The method as claimed in claim 12, wherein said silicon-containing compound(s) is one or more compounds selected from the group consisting of cyclomethicone, dimethicone, cyclomethicone/quaternium-18 hectorite, cyclomethicone polyol, dimethicone polyol, cetyl dimethicone copolyol, silica, phenyl methicone, phenyl dimethicone, and phenyl trimethicone and derivatives thereof.

25. The method as claimed in claim 11, wherein at least one hydroxy acid is gluconolactone.

26. The method as claimed in claim 11, wherein the alpha hydroxy acid is glycolic acid.

27. The method as claimed in claim 11, wherein the sunscreen agent is comprised of ultrafine particles of titanium dioxide coated with aluminum hydroxide and stearic acid.

28. The method as claimed in claim 11, wherein the sunscreen agent is comprised of ultrafine particles of zinc oxide coated with polymeric materials.

29. The method as claimed in claim 11, wherein the moisturizing agent(s) is selected from glycerin or butylene glycol.

30. The method as claimed in claim 11, wherein the antioxidant is vitamin E linoleate or vitamin E acetate.

31. The method as claimed in claim 11, wherein the cosmetically acceptable pigment is at least one C9–C15 polyfluoroalkyl treated iron oxide.

32. The method as claimed in claim 11, wherein the sunscreen agent is present in an amount sufficient to provide a sun protection factor of at least 15.

33. The method as claimed in claim 11, wherein the emulsifier is selected from one or more emulsifiers selected from the group consisting of dimethicone copolyol, sorbitan sesquioleate, PEG-30 dipolyhydroxystearate and cetyl dimethicone copolyol.

* * * * *